United States Patent
Kahn et al.

(10) Patent No.: US 8,864,663 B1
(45) Date of Patent: Oct. 21, 2014

(54) SYSTEM AND METHOD TO EVALUATE PHYSICAL CONDITION OF A USER

(75) Inventors: Philippe Kahn, Aptos, CA (US); Arthur Kinsolving, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 1382 days.

(21) Appl. No.: 11/366,041

(22) Filed: Mar. 1, 2006

(51) Int. Cl.
*A61B 5/00* (2006.01)
*A61B 5/11* (2006.01)
*A61B 5/145* (2006.01)
*G08B 21/02* (2006.01)
*A61B 5/024* (2006.01)
*G06F 19/00* (2011.01)
*G08B 21/00* (2006.01)

(52) U.S. Cl.
CPC .............. *G06F 19/34* (2013.01); *A61B 5/0002* (2013.01); *A61B 5/11* (2013.01); *A61B 5/1118* (2013.01); *A61B 5/14532* (2013.01); *G06F 19/3418* (2013.01); *G08B 21/0211* (2013.01); *A61B 5/024* (2013.01); *G06F 19/3481* (2013.01); *G08B 21/02* (2013.01); *A61B 2505/07* (2013.01); *Y10S 128/92* (2013.01)
USPC ........... 600/300; 600/301; 600/316; 600/481; 705/2; 705/3; 340/870.17; 340/539.12; 128/920; 702/19

(58) Field of Classification Search
CPC .... A61B 5/0002; A61B 5/024; A61B 5/1118; A61B 5/14532; G08B 21/02–21/0211; G06F 19/34–19/3481
USPC .......... 600/300–301, 316, 481; 128/903–905, 128/920–921; 705/2–4; 340/573.1–576, 340/870.17
See application file for complete search history.

(56) References Cited

U.S. PATENT DOCUMENTS

| 5,737,439 | A | 4/1998 | Lapsley et al. |
| 5,771,001 | A | 6/1998 | Cobb |
| 5,960,085 | A | 9/1999 | de la Huerga |
| 5,976,083 | A | 11/1999 | Richardson et al. |
| 5,989,200 | A | 11/1999 | Yoshimura et al. |
| 6,132,337 | A * | 10/2000 | Krupka et al. ................ 482/8 |

(Continued)

FOREIGN PATENT DOCUMENTS

| JP | 11347021 A | 12/1999 |
| WO | WO 02/088926 A1 | 11/2002 |

OTHER PUBLICATIONS

PCT Notification Preliminary Report on Patentability, PCT/US2006/29570, mailing date: Feb. 7, 2008, 6 pages.

(Continued)

*Primary Examiner* — William Thomson
*Assistant Examiner* — Marie Archer
(74) *Attorney, Agent, or Firm* — HIPLegal LLP; Judith A. Szepesi

(57) ABSTRACT

A system is provided to evaluate physical condition of a user based on the health data collected from one or more SMDs. The system may comprise a user data component, a routines component and a health status engine. The user data component may be configured to receive health data for the user. A routines component may be configured to identify a current routine associated with the health data. The health status engine may be configured to determine health status information based on the received health data and the identified current routine.

16 Claims, 7 Drawing Sheets

(56) References Cited

U.S. PATENT DOCUMENTS

| | | | |
|---|---|---|---|
| 6,241,684 B1* | 6/2001 | Amano et al. ............... | 600/531 |
| 6,408,330 B1 | 6/2002 | de la Huerga | |
| 6,493,652 B1 | 12/2002 | Ohlenbusch et al. | |
| 6,522,266 B1 | 2/2003 | Soehren et al. | |
| 6,595,929 B2* | 7/2003 | Stivoric et al. ............... | 600/549 |
| 6,786,866 B2* | 9/2004 | Odagiri et al. ............... | 600/300 |
| 6,788,980 B1 | 9/2004 | Johnson | |
| 6,813,582 B2 | 11/2004 | Levi et al. | |
| 6,898,550 B1 | 5/2005 | Blackadar et al. | |
| 6,990,660 B2 | 1/2006 | Moshir et al. | |
| 7,043,752 B2 | 5/2006 | Royer et al. | |
| 7,120,830 B2 | 10/2006 | Tonack | |
| 7,155,507 B2 | 12/2006 | Hirano et al. | |
| 7,353,179 B2 | 4/2008 | Ott et al. | |
| 7,379,999 B1 | 5/2008 | Zhou et al. | |
| 7,457,872 B2 | 11/2008 | Aton et al. | |
| 7,561,960 B2 | 7/2009 | Soehren | |
| 7,664,657 B1 | 2/2010 | Letzt et al. | |
| 2001/0053984 A1 | 12/2001 | Joyce et al. | |
| 2002/0016719 A1 | 2/2002 | Nemeth et al. | |
| 2002/0028988 A1* | 3/2002 | Suzuki et al. ............... | 600/300 |
| 2002/0138017 A1 | 9/2002 | Bui et al. | |
| 2003/0101260 A1 | 5/2003 | Dacier et al. | |
| 2003/0139908 A1 | 7/2003 | Wegerich et al. | |
| 2003/0149526 A1 | 8/2003 | Zhou et al. | |
| 2003/0196141 A1 | 10/2003 | Shaw | |
| 2003/0208113 A1 | 11/2003 | Mault et al. | |
| 2003/0227487 A1 | 12/2003 | Hugh | |
| 2003/0236625 A1 | 12/2003 | Brown et al. | |
| 2004/0017300 A1 | 1/2004 | Kotzin et al. | |
| 2004/0024846 A1 | 2/2004 | Randall et al. | |
| 2004/0043760 A1 | 3/2004 | Rosenfeld et al. | |
| 2004/0044493 A1 | 3/2004 | Coulthard | |
| 2004/0078219 A1 | 4/2004 | Kaylor et al. | |
| 2004/0078220 A1 | 4/2004 | Jackson | |
| 2004/0122294 A1 | 6/2004 | Hatlestad et al. | |
| 2004/0122295 A1 | 6/2004 | Hatlestad et al. | |
| 2004/0122296 A1 | 6/2004 | Hatlestad et al. | |
| 2004/0122297 A1 | 6/2004 | Stahmann et al. | |
| 2004/0122333 A1* | 6/2004 | Nissila ............... | 600/519 |
| 2004/0122484 A1 | 6/2004 | Hatlestad et al. | |
| 2004/0122485 A1 | 6/2004 | Stahmann et al. | |
| 2004/0122486 A1 | 6/2004 | Stahmann et al. | |
| 2004/0122487 A1 | 6/2004 | Hatlestad et al. | |
| 2004/0146048 A1 | 7/2004 | Cotte | |
| 2004/0148340 A1 | 7/2004 | Cotte | |
| 2004/0148341 A1 | 7/2004 | Cotte | |
| 2004/0148342 A1 | 7/2004 | Cotte | |
| 2004/0148351 A1 | 7/2004 | Cotte | |
| 2004/0148392 A1 | 7/2004 | Cotte | |
| 2004/0215755 A1 | 10/2004 | O'Neill | |
| 2004/0247748 A1 | 12/2004 | Bronkema | |
| 2004/0259494 A1 | 12/2004 | Mazar | |
| 2005/0027567 A1 | 2/2005 | Taha | |
| 2005/0033200 A1 | 2/2005 | Soehren et al. | |
| 2005/0038691 A1 | 2/2005 | Babu | |
| 2005/0054938 A1 | 3/2005 | Wehman et al. | |
| 2005/0079873 A1 | 4/2005 | Caspi et al. | |
| 2005/0101841 A9 | 5/2005 | Kaylor et al. | |
| 2005/0102167 A1 | 5/2005 | Kapoor | |
| 2005/0107944 A1 | 5/2005 | Hovestadt et al. | |
| 2005/0113650 A1 | 5/2005 | Pacione et al. | |
| 2005/0114502 A1 | 5/2005 | Raden et al. | |
| 2005/0131736 A1 | 6/2005 | Nelson et al. | |
| 2005/0146431 A1 | 7/2005 | Hastings et al. | |
| 2005/0182824 A1 | 8/2005 | Cotte | |
| 2005/0235058 A1 | 10/2005 | Rackus et al. | |
| 2005/0256414 A1* | 11/2005 | Kettunen et al. ............... | 600/509 |
| 2005/0262237 A1 | 11/2005 | Fulton et al. | |
| 2005/0272564 A1 | 12/2005 | Pyles et al. | |
| 2006/0020177 A1 | 1/2006 | Seo et al. | |
| 2006/0064020 A1 | 3/2006 | Burnes et al. | |
| 2006/0064276 A1 | 3/2006 | Ren et al. | |
| 2006/0109113 A1 | 5/2006 | Reyes et al. | |
| 2006/0154642 A1 | 7/2006 | Scannell, Jr. | |
| 2006/0161459 A9 | 7/2006 | Rosenfeld et al. | |
| 2006/0206587 A1 | 9/2006 | Fabbrocino | |
| 2006/0249683 A1 | 11/2006 | Goldberg et al. | |
| 2007/0017136 A1 | 1/2007 | Mosher et al. | |
| 2007/0024441 A1 | 2/2007 | Kahn et al. | |
| 2007/0050157 A1 | 3/2007 | Kahn et al. | |
| 2007/0067725 A1 | 3/2007 | Cahill et al. | |
| 2007/0073934 A1 | 3/2007 | Rogers | |
| 2007/0192483 A1 | 8/2007 | Rezvani et al. | |
| 2007/0239399 A1 | 10/2007 | Sheynblat et al. | |
| 2007/0260418 A1 | 11/2007 | Ladetto et al. | |
| 2008/0191608 A1 | 8/2008 | Schmidt et al. | |
| 2008/0254944 A1 | 10/2008 | Muri et al. | |
| 2009/0099668 A1 | 4/2009 | Lehman et al. | |

OTHER PUBLICATIONS

PCT International Search Report and the Written Opinion of the International Searching Authority, PCT/US2006/29570, mailing date Jul. 17, 2007, 7 pages.

\* cited by examiner

SYSTEM AND METHOD TO EVALUATE PHYSICAL CONDITION OF A USER

FIELD OF THE INVENTION

The present invention relates to virtual sensors, and in particular to a system and method to evaluate the physical condition of a user.

BACKGROUND

Electrical sensors, monitors, and devices built by an ever-changing group of manufacturers are constantly entering the market. Collectively, these devices will be referred to as SMDs (sensors, monitors, devices). SMDs may be capable of collecting data related to a user's health or physical condition, e.g., the blood pressure or heart rate of the user, and displaying this data to the user. The data related to a specific aspect of a user's physical condition (e.g., blood pressure) may be referred to as a physical condition parameter or health parameter.

Users are increasingly looking to utilize SMDs to monitor their health throughout their daily activities. In the prior art, remote access to data collected by SMDs has been limited to historical information, e.g., to information stored in databases or e-mails. However, the prior art systems do not analyze real time data collected from a user in order to provide an assessment of the user's physical (or health) condition.

For example, a particular heart rate of a person may, on one hand, indicate that the person is in the middle of a strenuous activity, e.g., playing rugby, or that a person is having an anxiety attack. Existing SMDs, while capable of displaying a value for a health parameter, are not capable of intelligently interpreting the value as indicative of a particular user's health state.

SUMMARY OF THE INVENTION

A method and system to evaluate the physical condition of a user are described. According to one aspect, the system comprises a real time user data component to receive physical condition parameter data for the user, a routines component to determine a routine for the user and a health status engine to determine health status information based on the received physical condition parameter data, utilizing the determined routine.

Other features of the present invention will be apparent from the accompanying drawings and from the detailed description that follows.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

As described in detail below, the technique introduced herein addresses issues associated with determining whether the real time data collected by various SMDs is indicative of a health problem for a particular person.

In one embodiment of the present invention, the health parameter values for a particular user are collected by an SMD (e.g., a heart rate monitor). The data collected by the SMD is communicated to processing center, e.g., a health server may store historical and current data that may be utilized to detect anomalies in the user's physical condition. The health server may store information related to the user's daily activities that may affect the SMD readings, such as medications intake, workouts, afternoon naps and so on. This information associated with a particular user may be organized as so called routines, where each routine comprises information related to events and activities that may affect SMD readings, as well as information regarding the expected changes in the SMD reading as the user goes about her daily activities.

When the health server receives SMD data related to a health parameter (e.g., the heart rate of the user), in one embodiment, the server may first select an applicable routine, analyze the received data utilizing information data regarding the expected changes in the user's heart rate throughout a period of time and, if the received SMD reading is outside the acceptable range of heart rate behavior for the user, generate and send an alert to the user. Thus, the method described herein may allow to differentiate between, for example, an increased heart rate caused by an aerobic activity and an increased heart rate caused by a heart attack.

In one embodiment, the present invention may be implemented in the context of a public network, e.g., a network that includes a health server that stores and analyzes health related data for the user. An example of such a network is illustrated in FIG. 1.

Figure 1:
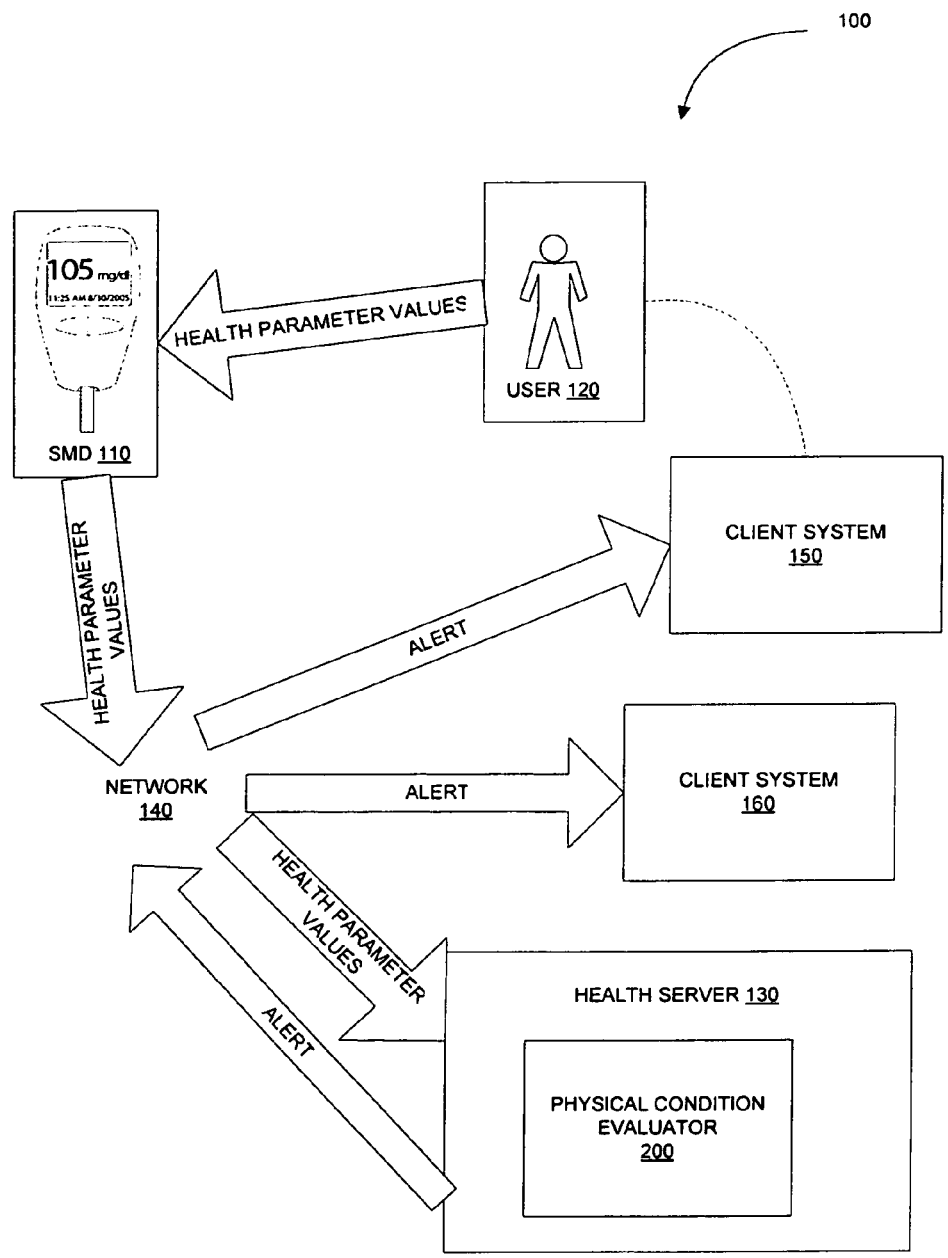
FIG. 1 is a network environment including a system to evaluate the physical condition of a user, according to one embodiment of the present invention.

FIG. 1 is a network environment including a system 100 to evaluate physical condition of a user, according to one embodiment of the present invention. The system 100 comprises one or more SMDs, such as a glucose monitor 110, to collect real time values from a user 120. The glucose monitor 110 may be in communication with a health server 130 via a communications network 140. The communications network 140, in one embodiment, may be a public network (e.g., the Internet). In another embodiment, the communications network is a cellular telephone network. The server 130 may comprise a physical condition evaluator 200, which may be configured to receive real time data from various SMDs, including the glucose monitor 110 and generate a health assessment for the user 120. The assessment may trigger one or more alerts that may be communicated to one or more clients, e.g., a client 150 associated with the user 110 and a client 160 associated with the user's physician. It will be noted, that a client processing system may be a general purpose computer, a mobile phone or any device capable of receiving an alert via a communications network.

In one embodiment, the physical condition evaluator 200 may be configured to communicate an alert to one or both of the client systems 150 an 160 when it is determined that the real time physical parameter data for the user is indicative of an unexpected health condition. For example, if the real time result of a glucose test for the user is determined by the evaluator 200 to be outside a predetermined acceptable range of behavior, the evaluator 200 may then generate and send an alert to the user 100 (e.g., by communicating the alert to the client 150 associated with the user). Some components of one embodiment of the physical condition evaluator 200 are illustrated in FIG. 2.

Figure 2:
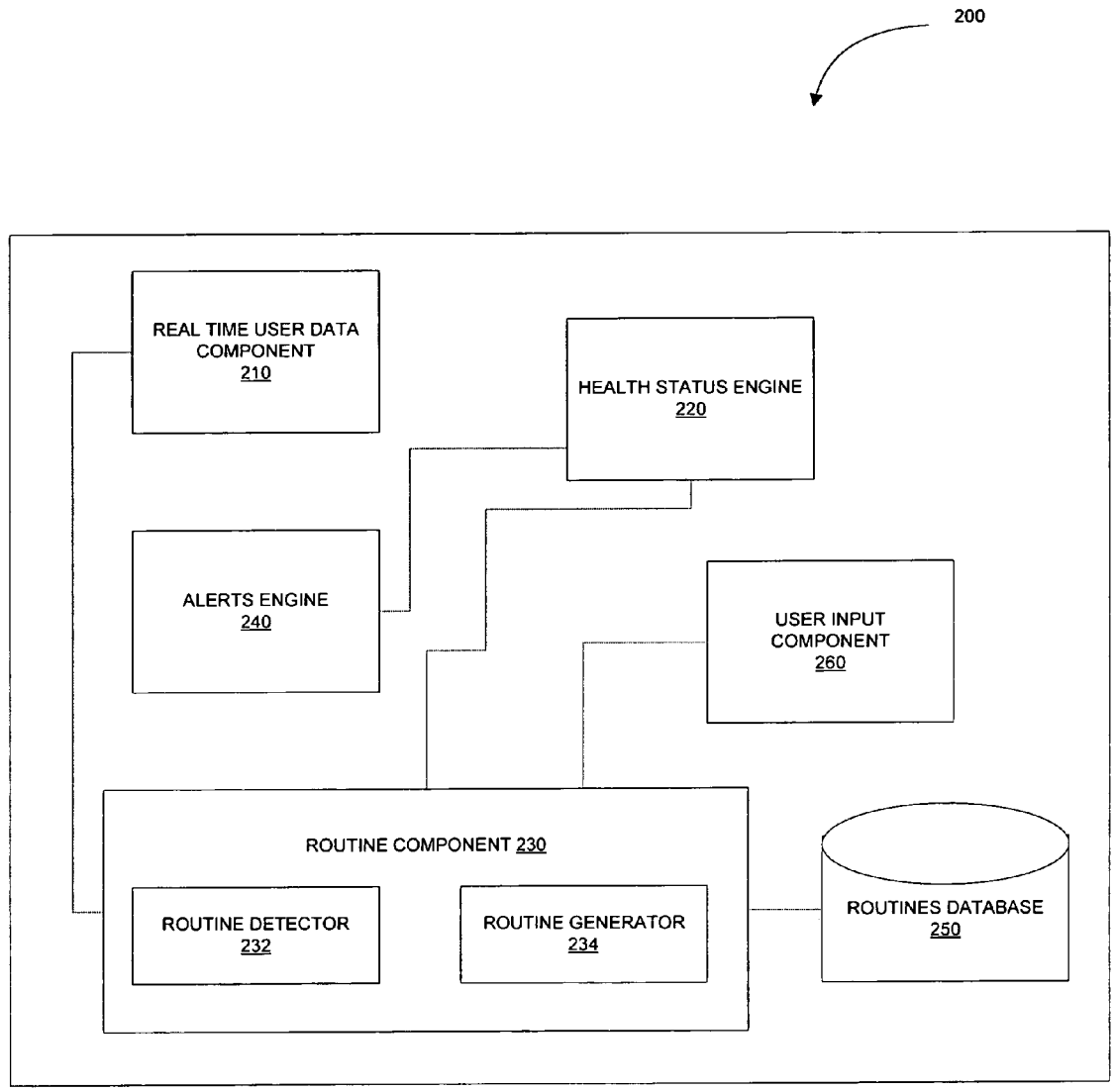
FIG. 2 is a block diagram illustrating various components of a physical condition evaluator, according to one embodiment of the present invention.

Referring to FIG. 2, the evaluator 200 comprises, in one embodiment, a real time user data component 210, a health status engine 220, a routine component 230, an alerts engine 240, a routines database 250 and a user input component 260. The real time user data component 210 may be configured to receive health parameter values for a user (e.g., data collected by the glucose meter 110), while the user input component 260 may be configured to receive information from the user, e.g., information regarding the user's daily activities. The health status engine 220, in turn, may be configured to determine the health status of the user utilizing one or more of the user's health routines that, in one embodiment, are stored in the routines database 250.

For the purposes of this description, a health routine (or simply a routine) will be understood as comprising expected behavior of one or more physical condition parameters (or health parameters) over a period of time. The behavior is defined by movement of the parameter with respect to time. For example, in one embodiment, a routine includes one or more of the following: actual values, rate of change in values, first order derivatives of the change (acceleration), as well as other measurements of the alteration of a parameter with respect to time. The expected health parameter behavior in a particular routine, in one embodiment, may be calculated taking into consideration the user's daily activities, any medications being taken by the user, as well as other information received by the user input component 260.

For example, during a day's activities a person's heart rate may fluctuate. For example, as a person walks to work every day their heart rate is higher than in the midafternoon when the person is sitting down. These changes form a consistent pattern for the user, but a pattern that may be different from all other people. Turning to another example, a person's blood sugar changes may follow the same general pattern from day to day under normal conditions. This expected movement of the values of the health parameter (e.g., maximum and minimum acceptable values, acceptable rates of change under certain conditions, etc.) may be utilized to generate a routine that can be used to evaluate the user's health data and is unique to that individual.

Returning to FIG. 2, the health status engine 220 cooperates with the routine component 230 to determine one or more applicable routines for processing the real time health parameter values for the user. In one embodiment, the routine component 230 comprises a routine detector 232 and a routine generator 234. If the routine detector 232 is unable to detect a routine for the real time health parameters (e.g., where a routine does not exist for this health parameter or none of the existing routines are applicable in view of the new information provided by the user regarding the user's activity or medications), the routine generator 234 may generate a new routine and store it in the routines database 250.

In one exemplary embodiment, the routines database 250 may also store a "healthy" routine for the user. The "healthy" routine may be generated based on the user's profile and may comprise information regarding the expected behavior of a variety of health parameters. For example, the "healthy" routine may comprise data such as maximum and minimum, mean, median and mode values, points of inflection for actual health parameter values, as well as for the rates of change for the various health parameters. In one embodiment, the acceptable ranges of values and rates of change for one health parameter may be determined in relation to one or more of other health parameters.

Returning to FIG. 2, as mentioned above, the health status engine 220 may first determine the health status for the user based on the real time health parameter values. In one embodiment, the health status engine 220 may then communicate the determined health status to the alerts engine 240 if the real time health parameter values deviate from the pattern in the applicable health routine more than a predetermined acceptable threshold. The alerts engine 240 may then generate one or more alerts. In one embodiment, an alert may result in a notification of the user, a notification of an appropriate third party, a notification of a government official or in triggering an action by the relevant SMD. For example, if the SMD is a blood sugar monitor, the alert may range from alerting the user to eat something, alerting the ambulance, to automatically injecting insulin or sugar into the user's bloodstream. Note that while the examples described herein are focused on health monitors, one of skill in the art would understand that similar patterns of behavior occur with respect to other types of monitors, such as environmental monitors.

The alert, in one embodiment, may be a visual, auditory, tactile or some other alert. In one embodiment, the alert may include the relevant data that triggered the alert, such as the user's blood sugar reading. In one embodiment, the alert may be a uniform resource locator (URL), which, when followed, may provide secure access to the relevant data on the server. In one embodiment, the alert may be an SMS message, Internet Instant message, a voicemail or any other type of notification that may be used to provide information.

Figure 3:
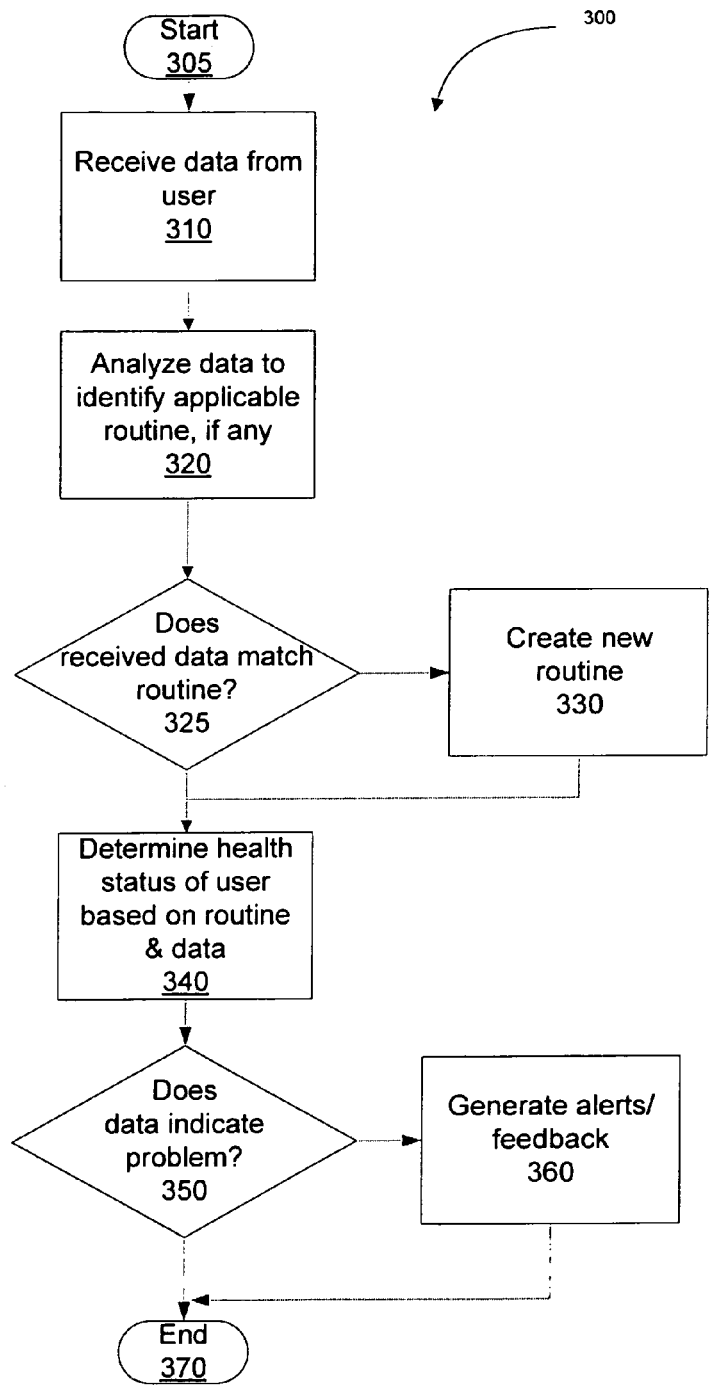
FIG. 3 is a flowchart of a method to evaluate the physical condition of a user, according to one embodiment of the present invention.

FIG. 3 is a flowchart of a method 300 to evaluate physical condition of a user, according to one embodiment of the present invention. The method may be performed by processing logic that may comprise hardware (e.g., dedicated logic, programmable logic, microcode, etc.), software (such as run on a general purpose computer system or a dedicated machine), or a combination of both. In one embodiment, the processing logic resides at the SIMS server 130 of FIG. 1A.

Referring to FIG. 3, the method 300 begins with the SIMS server 130 receiving data that is indicative of the user's health status (block 310). In one embodiment, the data, which may also be referred to as physical condition parameter data or health data, comprises SMD readings. In one embodiment, the data is real-time data. In another embodiment, the data may be collected over a period of time. At block 320, the processing logic analyzes the received data to determine an applicable routine that could be used to evaluate the user's physical condition. In one embodiment, the applicable routine is determined by the routine component 230. As described in further detail below, the routine component may detect an existing user routine or generate a new routine for the user based on the received data and additional user input, if available. At block 325, the process determines whether there is an existing user routine which matches the data. In one embodiment, past and current data is analyzed to identify routines. If the data does not match an existing user routine, the process continues to block 330. At block 330, the system generates a new routine. This is described in more detail below. The process then continues to block 340. If the existing routine was identified at block 325, the process continues directly to block 340.

At block 340, the determined applicable routine is, in one embodiment, utilized by the health status engine 220 to determine the health status (or physical condition) of the user based on the received real time data. At block 350, the process determines whether the user data requires an alert. Alerts are sent, in one embodiment, based on the health status of the user. If one or more alerts need to be sent, alerts engine 240 may selectively generate feedback for the user, based on the determined health status, at block 360. The process then ends.

One example of the above process is as follows. The data may comprise a person's heart rate readings collected by a heart rate monitor. Such readings may be collected over a period of 30 minutes and sent to the health server 130, may be sent real-time by the sensor, may be sent pseudo-real-time by the user, or may be entered by the user at various intervals. The health server 130 may then determine that the person is in the process of performing a strenuous physical activity, access an associated routine (e.g., a "work out" routine) for the person, and then compare the behavior (rates of change, second order rates of change, maximums and minimums, etc.) of the received heart rate data with the behavior indicated by the "work out" routine. If the real time data indicates that the person's heart rate is behaving outside the acceptable behavior indicated by the routine, for instance that the heart rate has been increasing more rapidly than an acceptable rate of increase, an alert may be sent via the health server to the person's mobile phone.

Figure 4:
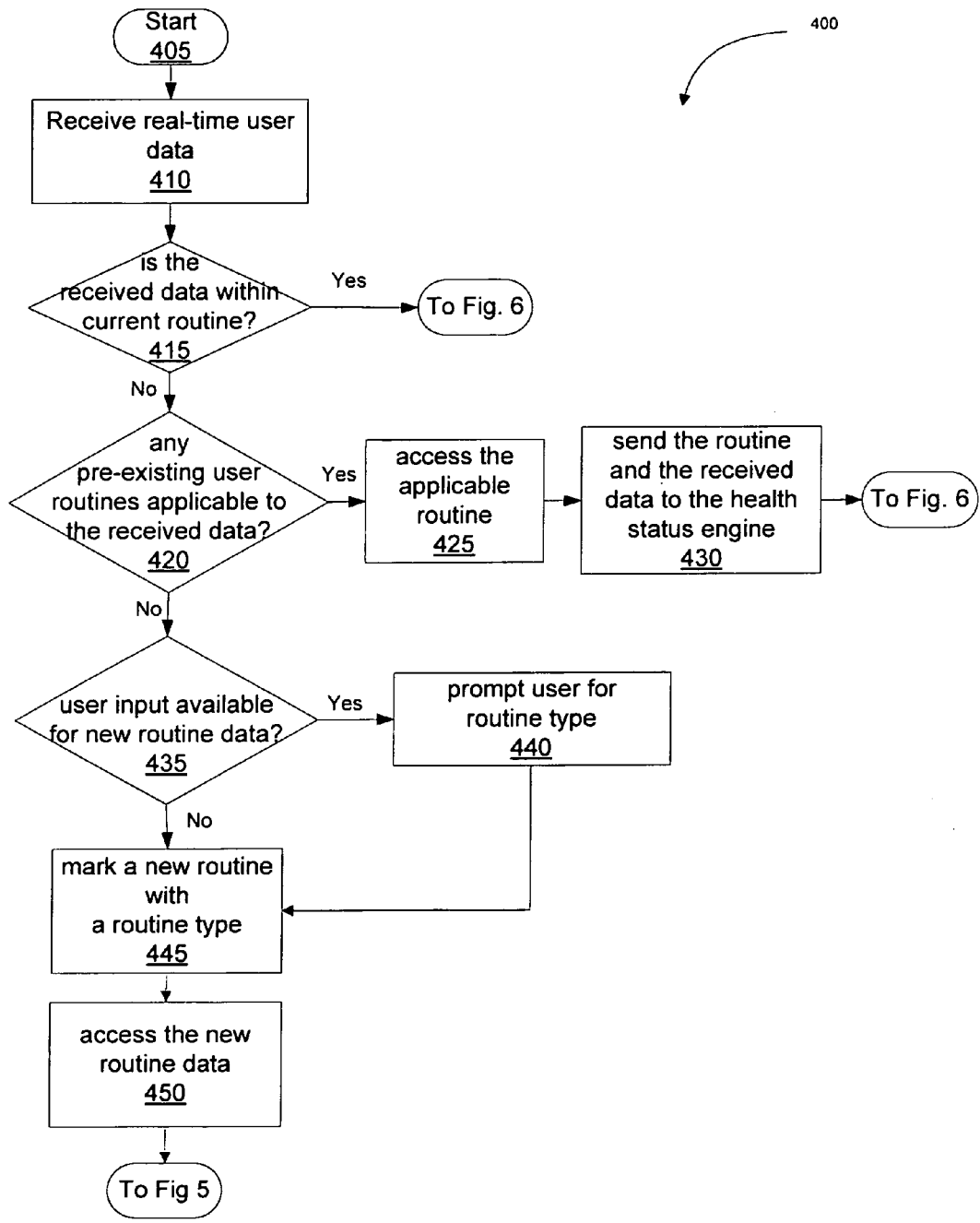
FIG. 4 is a flowchart of a method to determine an applicable routine to analyze health data, according to one embodiment of the present invention.

FIG. 4 is a flowchart of a method 400 to determine an applicable routine to analyze health data, according to one embodiment of the present invention. The method may be performed by processing logic that may comprise hardware (e.g., dedicated logic, programmable logic, microcode, etc.), software (such as run on a general purpose computer system or a dedicated machine), or a combination of both. In one embodiment, the processing logic resides at the SIMS server 130 of FIG. 1. Referring to FIG. 4, the method 400 begins at block 405. The health data is received at block 410 at the health server 130. At block 415, the routines component 230 of FIG. 2 determines whether the received health data is within the current routine. In one embodiment, the health server may be configured to maintain an indicator of the user's current routine. The current routine may be based on the explicit input provided by the user, based on the time of day, or based on the behavior of the user's health parameters. For example, the server may automatically determine that the user is performing their exercise routine A from the behavior of their heart rate and potentially the behavior of one or more other health parameters such as their blood pressure, pulse rate, blood sugar, etc. In another example, the server may receive a message from the user, notifying the server that the user is about to play beach volleyball. Based on this input, the server may set the current routine during that indicated period to an existing "heart rate during aerobic activity" routine.

Returning to FIG. 4, if it is determined that the real time data is within the current routine (e.g., if the real time data is the user's heart rate readings comprises the expected heart rate behavior in accordance with the current routine) the control passes to the health status engine, as will be described in further detail with reference to FIG. 6.

If it is determined that the real time data is not within the current routine (e.g., if the real time data does not match the expected behavior according to the current routine) the routine detector 232 of the routines component 230 detects whether an applicable routine exists (block 420) and, if so, accesses the detected routine (block 425). The detected routine and the received health data are then passed to the health status engine 220 (block 430), where the health data is analyzed, as will be described in further detail with reference to FIG. 6.

If it is determined, at block 420, that there is no existing routine that is applicable to analyze the received health data, the process—in one embodiment performed by the routine generator 234 of the routine component 230—determines, at block 425, whether any user data is available for generating new routine data. User data may include user input, indicating an activity, user health data and "generic" activity definitions, or other data. If such data is not available, the user may be prompted, at block 430, to identify a routine type associated with the current data. A routine type may be designated as, for example, "rest" or "work out" for routines that define expected ranges of values for heart rate, blood pressure, glucose levels, etc. If no user input is available, the routine generator 234 may use a default routine type. The method 400 then continues to block 435, where a new routine is marked with the routine type.

The new routine data is accessed at block 440 to be utilized for generating the new routine. Further details regarding generating a new routine are discussed with reference to FIG. 5.

Figure 5:
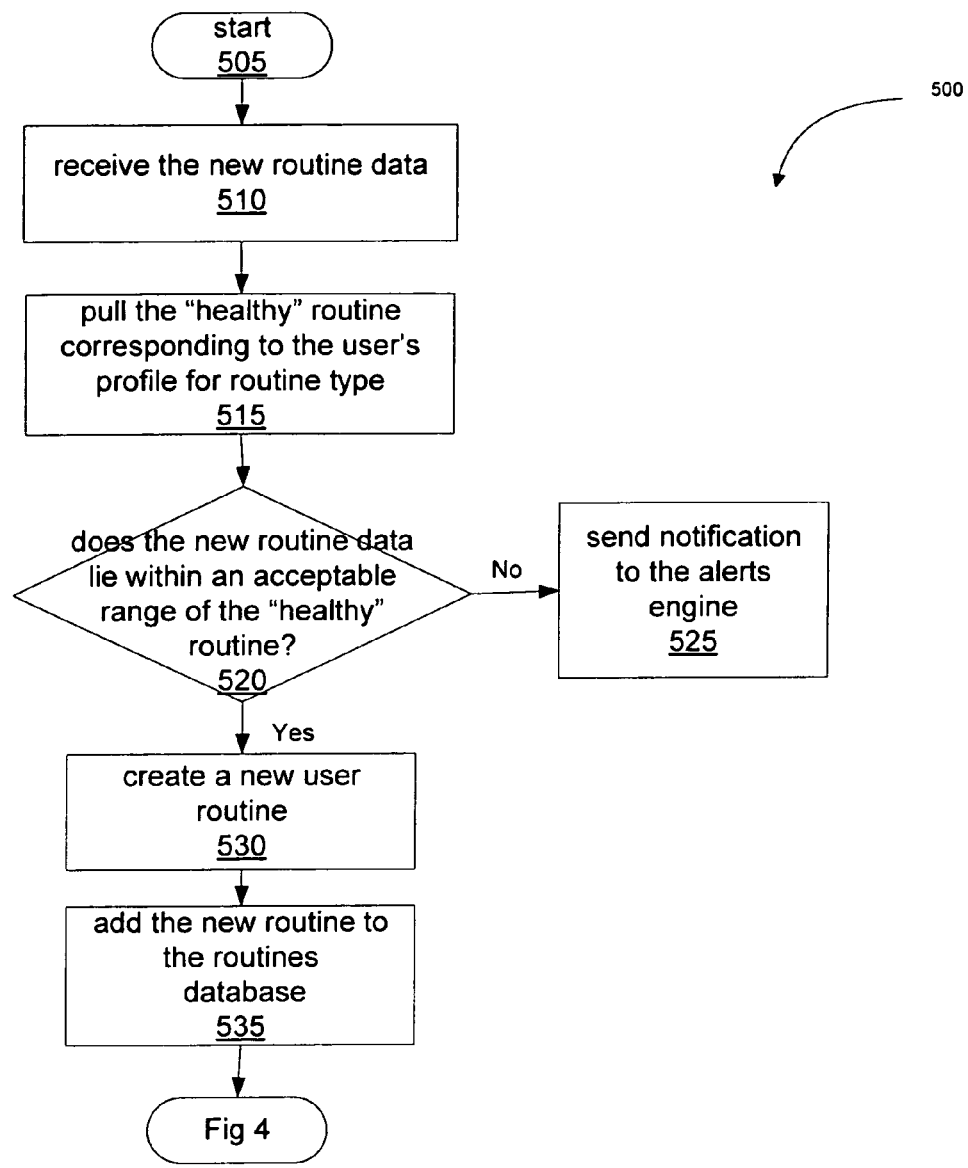
FIG. 5 is a flowchart of a method to generate a new routine for a user, according to one embodiment of the present invention.

FIG. 5 is a flowchart of a method 500 to generate a new routine for a user, according to one embodiment of the present invention. The method may be performed by processing logic that may comprise hardware (e.g., dedicated logic, programmable logic, microcode, etc.), software (such as run on a general purpose computer system or a dedicated machine), or a combination of both. In one embodiment, the processing logic resides at the health server 130 of FIG. 1.

Referring to FIG. 5, the method 500 begins at block 505. The new routine generator 234 receives the new routine data at block 510 and then pulls an appropriate generic "healthy" routine from the routines database 250 (block 515). In one embodiment, the "healthy routine" for a user may be adjusted based on the user's known parameters. For example, for a new routine of "vigorous exercise" the expected heart rates and blood pressure values for a serious athlete would be significantly different from values for a weekend warrior. The system creates a user-adjusted "healthy" routine. The new routine generator 234 next analyzes the new data in view of the user-adjusted "healthy" routine. If it is determined, at block 520, that the new data lies within an acceptable range of values and within acceptable rates of change indicated in the "healthy" routine, the new routine generator 234 creates a new routine for the user (block 530) and adds the new routine to the routines database 250 (block 535). The method may continue, as described above with reference to FIG. 4.

If it is determined, at block 520, that the new routine data does not lie within an acceptable range of values and within acceptable rates of change indicated in the "healthy" routine, the control is passed to the alerts engine 240. The alerts engine 240 may, in turn, generate one or more alerts and communicate the alerts to the user or to any relevant parties. Additional details regarding techniques to generate and send alerts are discussed in co-pending U.S. patent application Ser. No. 11/192,549, filed Jul. 29, 2005, entitled "Monitor, Alert, Control, and Share (MACS) System," which is herein incorporated by reference.

Figure 6:
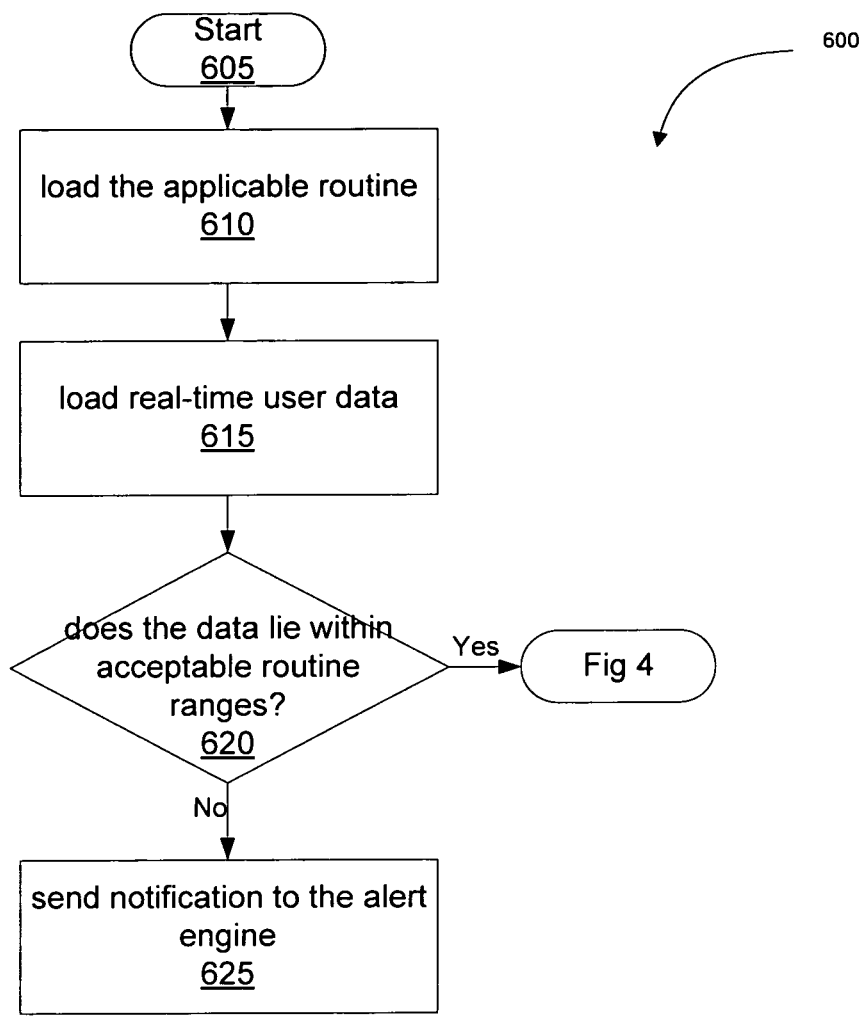
FIG. 6 is a flowchart of a method to determine health status for a user, according to one embodiment of the present invention.

FIG. 6 is a flowchart of a method 600 to determine health status for a user, according to one embodiment of the present invention. In one embodiment, this process is performed automatically once new data has been associated with a particular user routine. The method may be performed by processing logic that may comprise hardware (e.g., dedicated logic, programmable logic, microcode, etc.), software (such as run on a general purpose computer system or a dedicated machine), or a combination of both. In one embodiment, the processing logic resides at the health server 130 of FIG. 1.

Referring to FIG. 6, the method 600 begins at block 605. The health status engine 220 uses the applicable routine (block 610) and the real time health data for the user (block 615). If it is determined, at block 615, that the health data lies outside of the acceptable health parameter behavior with respect to absolute or relative health parameter behaviors that are dictated by the applicable routine, the health status engine 220 may communicate this information to the alerts engine 240 at block 620.

The alerts engine 220, in turn, may generate and send one or more alerts to the user or any relevant parties. As mentioned above, details regarding techniques to generate and send alerts are discussed in U.S. patent application Ser. No. 11/192,549, filed Jul. 29, 2005.

If it is determined, at block 615, that the health data lies within the acceptable health parameter behaviors, the method may continue, as described above with reference to FIG. 4.

It will be noted, that while these processes are described using flowcharts, in actuality, the implementation may be interrupt driven. In one embodiment, each data connection with an actual SMD may trigger a separate thread on the server in order to perform these functions.

Figure 7:
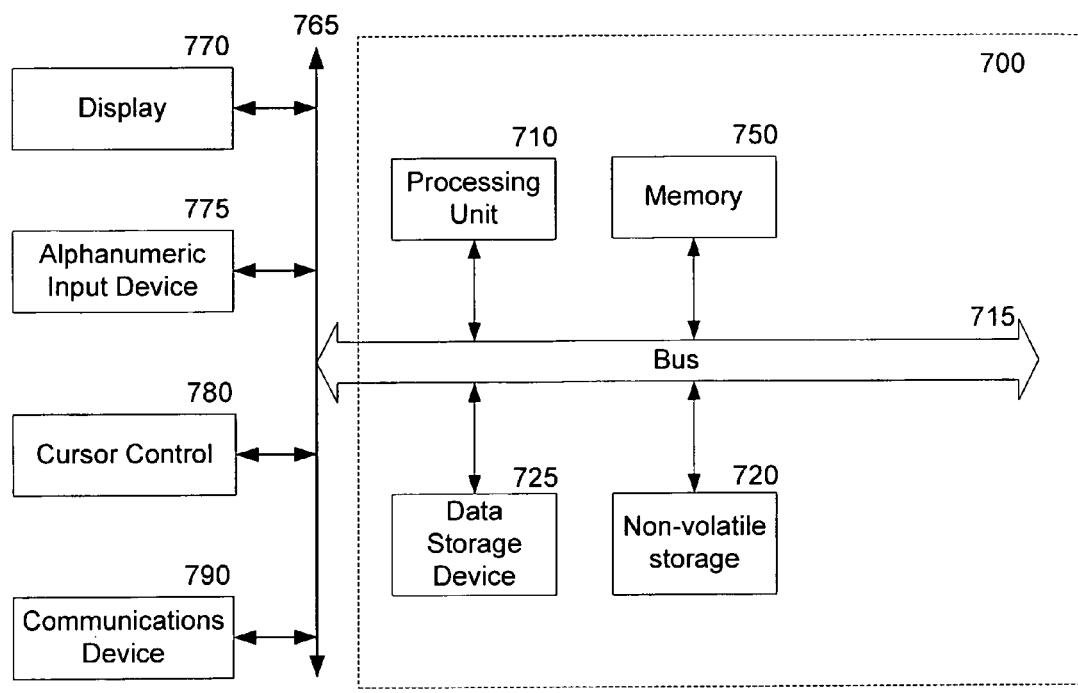
FIG. 7 is a diagrammatic representation of a computer system, within which a set of instructions, for causing the machine to perform any one or more of the methodologies discussed herein, may be executed.

FIG. 7 is a block diagram of a computer system on which the software of the present invention may be implemented. It will be apparent to those of ordinary skill in the art, however that other alternative systems of various system architectures may also be used.

The data processing system illustrated in FIG. 7 includes a bus or other internal communication means 745 for communicating information, and a processor 740 coupled to the bus 745 for processing information. The system further comprises a random access memory (RAM) or other volatile storage device 750 (referred to as memory), coupled to bus 745 for storing information and instructions to be executed by processor 740. Main memory 750 also may be used for storing temporary variables or other intermediate information during execution of instructions by processor 740. The system also comprises a read only memory (ROM) and/or static storage device 720 coupled to bus 740 for storing static information and instructions for processor 740, and a data storage device 725 such as a magnetic disk or optical disk and its corresponding disk drive. Data storage device 725 is coupled to bus 745 for storing information and instructions.

The system may further be coupled to a display device 770, such as a cathode ray tube (CRT) or a liquid crystal display (LCD) coupled to bus 745 through bus 765 for displaying information to a computer user. An alphanumeric input device 775, including alphanumeric and other keys, may also be coupled to bus 745 through bus 765 for communicating information and command selections to processor 740. An additional user input device is cursor control device 780, such as a mouse, a trackball, stylus, or cursor direction keys coupled to bus 745 through bus 765 for communicating direction information and command selections to processor 740, and for controlling cursor movement on display device 770.

Another device, which may optionally be coupled to computer system 730, is a communication device 790 for accessing other nodes of a distributed system via a network. The communication device 790 may include any of a number of commercially available networking peripheral devices such as those used for coupling to an Ethernet, token ring, Internet, or wide area network. Note that any or all of the components of this system illustrated in FIG. 7 and associated hardware may be used in various embodiments of the present invention.

It will be appreciated by those of ordinary skill in the art that any configuration of the system may be used for various purposes according to the particular implementation. The control logic or software implementing the present invention can be stored in main memory 750, mass storage device 725, or other storage medium locally or remotely accessible to processor 740. Other storage media may include floppy disks, memory cards, flash memory, or CD-ROM drives.

It will be apparent to those of ordinary skill in the art that the methods and processes described herein can be implemented as software stored in main memory 750 or read only memory 720 and executed by processor 740. This control logic or software may also be resident on an article of manufacture comprising a computer readable medium having computer readable program code embodied therein and being readable by the mass storage device 725 and for causing the processor 740 to operate in accordance with the methods and teachings herein.

The software of the present invention may also be embodied in a handheld or portable device containing a subset of the computer hardware components described above. For example, the handheld device may be configured to contain only the bus 745, the processor 740, and memory 750 and/or 725. The handheld device may also be configured to include a set of buttons or input signaling components with which a user may select from a set of available options. The handheld device may also be configured to include an output apparatus such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A computer system to evaluate a health condition of a user, the system comprising:
    a processor to generate a personalized routine for the user based on health data of the user;
    a memory to store the personalized routine for the user in a data store that includes a plurality of routines;
    the processor to select the personalized routine from among the plurality of routines based on the health data of the user,
    the personalized routine including expected behavior of one or more physical condition parameters for the user based on the health data of the user, the expected behavior including a range and a rate of change of one or more physical condition parameters,
    wherein each of the plurality of routines includes different expected behavior of the one or more physical condition parameters for the user;
    the processor to execute a user data component to receive digital data representing current health data for the user from a sensor, monitor or device (SMD), the current health data including a plurality of physical condition parameters for the user;

the processor to execute a routines component to analyze the received digital data to identify a new personalized routine to use for evaluating a physical condition of the user from the plurality of routines, based on the current health data;

the processor to execute a health status engine to monitor the physical condition parameters of the user, and to determine whether the current health data lies within the expected behavior of the one or more physical condition parameters of the new personalized routine, the expected behavior including the range and the rate of change of the physical parameters; and the processor to execute an alerts engine to communicate an alert when it is determined that the current health data lies outside the expected behavior of the one or more physical condition parameters of the new personalized routine.

2. The system of claim 1, wherein the current health data comprises one or more of: heart rate and blood sugar level.

3. The system of claim 1, wherein the expected behavior of the one or more physical condition parameters include acceptable current physical condition parameter values and acceptable rates of changes for the physical condition parameter values, wherein
the health status engine determines current rates of changes for the physical condition parameter values and determine deviation of the current rates of changes from rates of changes associated with the routine.

4. The system of claim 1, wherein the one or more physical condition parameters include one or more of the following: maximum and minimum values, first and second derivatives, and other measurements of the movement of a variable with respect to time.

5. The system of claim 1, further comprising:
the user data component to receive an indicator of a current user activity, wherein the routine component to use the current user activity to identify the personalized routine, the personalized routine being associated with at least one activity of the user.

6. The system of claim 1, wherein the health status engine to compute a first derivative or an approximation of a first derivative of a physical condition parameter with respect to time to determine a rate of change of the physical condition parameter, the health status engine further to compare the rate of change of the physical condition parameter to an acceptable rate of change for that physical condition parameter.

7. The system of claim 1, the system further comprising:
the processor to execute the user data component to receive the health data; and
the processor to execute a routine generator to generate the personalized routine for the user based on the health data.

8. A non-transitory machine-readable medium having stored thereon data representing sets of instructions which, when executed by a machine, cause the machine to:
generate a personalized routine for the user based on physical condition parameter data for the user;
store a personalized routine for a user in a data store that includes a plurality of routines;
select the personalized routine from among the plurality of routines based on the physical condition parameter data for the user,
the personalized routine including expected behavior of one or more physical condition parameters for the user based on the physical condition parameter data of the user, wherein each of the plurality of routines includes different expected behavior of the one or more physical condition parameters for the user;
receive additional physical condition parameter data for the user from a sensor, monitor or device (SMD);
analyze the received additional physical condition parameter data to select a new personalized routine to use for evaluating a physical condition of the user from the plurality of routines;
monitor the user's physical condition parameter data, for the new personalized routine, including the expected behavior of the one or more physical condition parameters for the user, the expected behavior comprising ranges and rates of change of the physical condition parameters for the user;
determine health status information based on a comparison of the received additional physical condition parameter data to the expected behavior of the one or more physical condition parameters for the user of the new personalized routine; and
communicate an alert when the health status information indicates a health problem for the user.

9. The non-transitory machine-readable medium of claim 8, wherein the determination includes computing a first derivative or an approximation of a first derivative of a physical condition parameter with respect to time to determine a rate of change of the physical condition parameter and comparing the rate of change of the physical condition parameter to an acceptable rate of change for that physical condition parameter.

10. The non-transitory machine-readable medium of claim 8, the method further comprising the instructions to cause the machine to:
receive the previous physical condition parameter data for the user; and
generate the personalized routine for the user based on the physical condition parameter data.

11. A computer system comprising:
a processor to execute a routines component to identify a personalized routine to use for evaluating a physical condition of a user from a plurality of routines based on received physical condition parameter data, the received physical condition parameter data received from one or more sensors associated with the user, wherein each of the plurality of routines is associated with a distinct physical activity level, and wherein each of the plurality of routines includes different acceptable ranges and acceptable rates of change for one or more physical condition parameters for the user;
the processor to execute a health status engine to determine whether the physical condition parameter data associated with the user is within acceptable ranges for the personalized routine, the health status engine to compute a first derivative or an approximation of a first derivative of the physical condition parameter with respect to time to determine a rate of change of the physical condition parameter, the health status engine further to compare the rate of change of the physical condition parameter to the acceptable rate of change for the received physical condition parameter; and
the processor to execute an alerts engine to communicate an alert when it is determined that the additional physical condition parameter data lies outside the acceptable ranges for the personalized routine, wherein the communication of the alert is via one or more of: a visual display to output a visual alert, a speaker to output an auditory alert, a vibrating mechanism to output a tactile alert, a control message to a device, and a message sent via a network to a third party.

12. The system of claim 11, wherein the personalized routine comprises one of the following: rest, light activity, medium activity, sports activity, vigorous sports activity.

13. The system of claim 11, wherein the physical condition parameters comprise one or more of the following: heart rate detected with a heart rate monitor, blood glucose level detected with a glucose monitor, and blood pressure.

14. The system of claim 11, wherein the personalized routine is identified based on motion data.

15. The system of claim 11, wherein the physical parameters comprise one or more of the following: maximum and minimum values, first and second derivatives, and other measurements of the movement of a variable with respect to time.

16. The system of claim 11, wherein the one or more physical parameters comprise a heart rate.

\* \* \* \* \*